(12) United States Patent
Ouwerkerk et al.

(10) Patent No.: US 10,405,761 B2
(45) Date of Patent: Sep. 10, 2019

(54) DEVICE FOR DETECTING HEART RATE AND HEART RATE VARIABILITY

(71) Applicant: KONINKLIJKE PHILIPS N.V., Eindhoven (NL)

(72) Inventors: Martin Ouwerkerk, Culemborg (NL); Stefan Van De Pas, Herten (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 13 days.

(21) Appl. No.: 15/549,244

(22) PCT Filed: Feb. 16, 2016

(86) PCT No.: PCT/IB2016/050805
§ 371 (c)(1),
(2) Date: Aug. 7, 2017

(87) PCT Pub. No.: WO2016/135583
PCT Pub. Date: Sep. 1, 2016

(65) Prior Publication Data
US 2018/0028080 A1    Feb. 1, 2018

Related U.S. Application Data

(60) Provisional application No. 62/119,977, filed on Feb. 24, 2015, provisional application No. 62/265,437, filed on Dec. 10, 2015.

(51) Int. Cl.
*A61B 5/024*     (2006.01)
*A61B 5/00*      (2006.01)
(Continued)

(52) U.S. Cl.
CPC ........ *A61B 5/02416* (2013.01); *A61B 5/0245* (2013.01); *A61B 5/02405* (2013.01);
(Continued)

(58) Field of Classification Search
CPC .................. A61B 5/02416; A61B 5/02405
(Continued)

(56) References Cited

U.S. PATENT DOCUMENTS

2003/0166996 A1    9/2003   Kim
2008/0165017 A1    7/2008   Schwartz
(Continued)

FOREIGN PATENT DOCUMENTS

EP    2319410 A1    5/2011
EP    2696754 B1    9/2014
(Continued)

OTHER PUBLICATIONS

Dishman,RK et al., "Cardiorespiratory Fitness and Laboratory Stress: a Meta-Regression Analysis", Psychophysiology 2006;43:57-72.
(Continued)

*Primary Examiner* — Nadia A Mahmood
(74) *Attorney, Agent, or Firm* — Sherry Austin

(57) ABSTRACT

One or more sensors and/or sensing techniques are used individually or in combination to detect and/or measure heart rate and/or heart rate variability. The sensors may be wearable and/or portable and may operate on different principles and may include different power profiles. The sensors and/or sensing techniques may be used at the same time or at different times that may overlap partially or completely, or may be mutually exclusive. A controller may select one or more sensors and/or sensing techniques based on operating conditions and/or based on conservation of power.

20 Claims, 5 Drawing Sheets

(51) Int. Cl.
*A61B 5/0245* (2006.01)
*A61B 5/053* (2006.01)

(52) U.S. Cl.
CPC ............ *A61B 5/0531* (2013.01); *A61B 5/681* (2013.01); *A61B 5/7207* (2013.01); *A61B 2560/0209* (2013.01)

(58) Field of Classification Search
USPC ........................................................ 600/508
See application file for complete search history.

(56) References Cited

U.S. PATENT DOCUMENTS

| | | | |
|---|---|---|---|
| 2010/0268056 A1* | 10/2010 | Picard | A61B 5/0531 600/300 |
| 2012/0123232 A1 | 5/2012 | Najarian | |
| 2014/0031704 A1 | 1/2014 | DeVries | |
| 2014/0094675 A1 | 4/2014 | Luna | |
| 2014/0273858 A1 | 9/2014 | Panther | |
| 2014/0358012 A1 | 12/2014 | Richards | |

FOREIGN PATENT DOCUMENTS

| | | | |
|---|---|---|---|
| KR | 20100132592 A | 12/2010 | |
| WO | WO2012140537 A1 | 10/2012 | |
| WO | WO2014147024 A1 | 9/2014 | |
| WO | WO2016050551 A1 | 4/2016 | |

OTHER PUBLICATIONS

Hamer, M et al., "Association Between Physical Fitness, Parasympathetic Control, and Proinflammatory Responses to Mental Stress", Psychosomatic Medicine, 69: 660-666, 2007.
http://www.nlm.nih.gov/medlineplus/ency/article/003877.htm Web-page downloaded from the Internet Jul. 26, 2017.
http://www.mioglobal.com Web-page downloaded from the Internet Jul. 26, 2017.
http://www.tomtom.com Web-page downloaded from the Internet Jul. 26, 2017.
http://www.mybasis.com Web-page downloaded from the Internet Jul. 26, 2017.
Schafer, A. et al., "How Accurate is Pulse Rate Variability as an Estimate of Heart Rate Variability? A Review on Studies Comparing Photoplethysmographic Technology with an Electrocardiogram", International Journey of Cardiology, vol. 166, 2013, pp. 15-29.
Van Der Zwaag, M.D. et al., "Reading the Human in the Driver Seat", Proceedings VISION 2014, Versailles, France, Oct. 14-15, 2014, pp. 1-8.
PCT International Search Report, International application No. PCT/IB2016/050805, dated May 4, 2016.

* cited by examiner

DEVICE FOR DETECTING HEART RATE AND HEART RATE VARIABILITY

CROSS-REFERENCE TO RELATED APPLICATIONS

This patent application claims the priority benefit under 35 U.S.C. § 371 of international patent application no. PCT/IB2016/050805 filed Feb. 16, 2016, which claims the benefit of U.S. Application Ser. No. 62/119,977, filed on Feb. 24, 2015 and of U.S. Application Ser. No. 62/265,437, filed on Dec. 10, 2015. These applications are hereby incorporated by reference herein in their entirety.

TECHNICAL FIELD

The present disclosure relates to methods and apparatuses for detecting heart rate and/or heart rate variability.

BACKGROUND

Heart rate (HR) and heart rate variability (HRV) are measurable quantities that help to assess the health and/or fitness of a living subject. For example, HRV measurements may be used in the detection of stress in humans. One device used to measure or obtain these parameters is a photoplethysmograph (PPG), which illuminates skin and detects changes in skin volume by inspecting transmitted or reflected light. Changes in volume caused by skin or blood vessels being enlarged or shrunk by heart beats can be measured to detect the heart beats. The HR and/or HRV can be determined from the detection of heart beats and intervals between heart beats, sometimes referred to as an inter-beat interval (IBI). PPG devices can be relatively compact, and can be portable or can be worn by an individual subject.

When a living subject is in motion, the accuracy of a PPG device is diminished. Noise in the form of motion artifacts is introduced in the sensor readings. Accordingly, it may be difficult to reliably measure or obtain the IBI of a subject in motion using a PPG device. Robust measurement of HRV becomes challenging in such circumstances.

Artifacts introduced by movement can partially be countered by increasing the light output of the light source in the PPG device. High power use of the light source in this manner causes the battery life of these wrist-worn PPG devices to be significantly reduced.

Artifacts may also be countered with the use of accelerometers that can detect motion of the PPG device and provide compensation estimates for signals obtained from the PPG device. However, use of one or more accelerometers to detect motion for motion artifact compensation tends to increase cost, size and power consumption of the overall device.

Another technique that can be used to measure HR and HRV is based on skin conductance (SC). An SC-based device measures electrical characteristics of an area of skin to determine various quantities of interest, including HR and/or HRV. For example, during physical activity, SC is attenuated by the beating of the heart, which permits detection of HR and/or HRV. However, SC devices sometimes encounter accuracy challenges in the absence of physical activity.

SUMMARY

This summary is provided to introduce a selection of concepts in a simplified form that are further described below in the Detailed Description section. This summary is not intended to identify key features or essential features of the claimed subject matter, nor is it intended to be used as an aid in determining the scope of the claimed subject matter.

The techniques and implementations discussed herein relate to methods and apparatuses for sensing cardiac or cardiovascular events in a subject entity. In particular, detection and/or measurement of heartbeats, heart rate (HR) and/or heart rate variability (HRV) is discussed. One or more sensors or sensing techniques may be employed to detect and/or measure these quantities, and the sensor(s) may be wearable and/or portable. The sensor(s) may operate using a limited power source, such as one or more batteries, a solar energy power source, or any other type of portable or wearable power source. The sensors and/or sensing techniques may operate on different principles and may include different power profiles. The sensors and/or sensing techniques may be used at the same time or at different times that may overlap partially or completely, or may be mutually exclusive.

A controller may be employed to provide communication and/or control functions for the sensors and/or sensing techniques. The controller may be implemented as a processor that accesses instructions from storage and executes the instructions to carry out communication and/or control functions. The controller may be analog or digital and may include a number of components such as storage, input/output control and/or management, one or more central processing units and/or arithmetic processing units, a communication interface, a user interface, and may include other components that contribute to implementing methods and/or apparatuses in accordance with the present disclosure. The controller may be sufficiently small to be portable or worn by an individual.

The methods and/or apparatuses according to the present disclosure may be implemented with a wearable device for detecting HR and/or HRV. According to some embodiments, the device may be worn on an appendage of the subject, such as on a human wrist. The device may include one or more photoplethysmograph (PPG) sensors and/or one or more skin conductance (SC) sensors. The PPG sensor(s) and/or SC sensor(s) may have ranges of operation that are the same, at least partially overlapping and/or mutually exclusive or non-overlapping, for the same or different types of sensors collectively. According to an example, one or more PPG sensors are used to detect heartbeats during periods of low activity of the subject. According to another example, one or more SC sensors are used to detect heartbeats during high activity periods of the subject. The PPG sensor may consume more energy than the SC sensor during active heartbeat detection.

According to some embodiments, the controller controls the PPG sensor(s) and/or the SC sensor(s) to detect HR and/or HRV over different ranges of physical activity or conditions of a subject being monitored by the sensor(s). For example the controller may turn on or turn off one or more sensors. The controller may provide signaling to the sensor(s) to cause the sensors to change their range of operation, for example by causing the sensor(s) to be more or less sensitive to certain phenomena that may impact detection of HR and/or HRV. The controller may use the data obtained from the sensor(s) to determine HR and/or HRV, and so may selectively use data from one or more sensors. The selection of data from one or more sensors may include turning a sensor on or off, putting a sensor in a lower or higher power mode, blocking or receiving data from a sensor, applying different algorithms to condition or analyze data from a sensor, or any other action that causes data to be selectively obtained from one or more sensors. The selection of data from one or more sensors may be based on signal quality of the signals provided by the sensor(s). Other criteria for selection may be derived from other sources, such as one or more accelerometers, time of day, table lookup or algorithm application for sensor signals with certain characteristics, and any other source that may indicate a preference for a certain sensing technique or a sensor to obtain useful data to detect or determine HR and/or HRV.

According to some embodiments, an accelerometer may be used or not. For example, an accelerometer may be present in an embodiment of the disclosed apparatus or not, or may be present and turned on or off. According to some configurations, an accelerometer is not used to switch sensors or to reduce motion artifacts. The controller may execute instructions (software), in accordance with an algorithm, to assess signal quality from a given sensor and may select one sensor over the other to measure heartbeats. The controller may also or otherwise control sensor usage or implement sensing techniques to reduce battery power consumption.

The disclosed methods and/or apparatuses may measure SC with relatively high precision and/or at a relatively high rate. An SC sensor may include skin sensing electronics, an anti-aliasing filter and/or a balanced floating design. The controller and/or SC sensor may include filtering of the raw sensor signal, and may include a digital filter for the analog to digital converter output. A signal may be obtained from the SC sensor that yields a waveform from which peaks caused by the heartbeats can be extracted. HR and/or HRV may be obtained from the timestamps of the peaks. An SC sensor is shown in European patent application no. 14 18 6956, the entire disclosure of which is hereby incorporated herein by reference.

According to an embodiment, the data related to HR and/or HRV may be stored, for example using a micro SD card, and/or may be transmitted, for example via a Bluetooth link, to a receiving station such as a mobile phone or other communication/network device.

These and other features and advantages, which characterize the present non-limiting embodiments, will be apparent from a reading of the following detailed description and a review of the associated drawings. It is to be understood that both the foregoing general description and the following detailed description are explanatory only and are not restrictive of the non-limiting embodiments as claimed.

BRIEF DESCRIPTION OF DRAWINGS

The methods and apparatuses of the present disclosure are discussed in greater detail below. Non-limiting and non-exhaustive examples are described with reference to the accompanying drawings, in which.

In the drawings, like reference characters generally refer to corresponding parts throughout the different views. The drawings are not necessarily to scale, emphasis instead being placed on the principles and concepts of operation.

DETAILED DESCRIPTION

Figure 1:
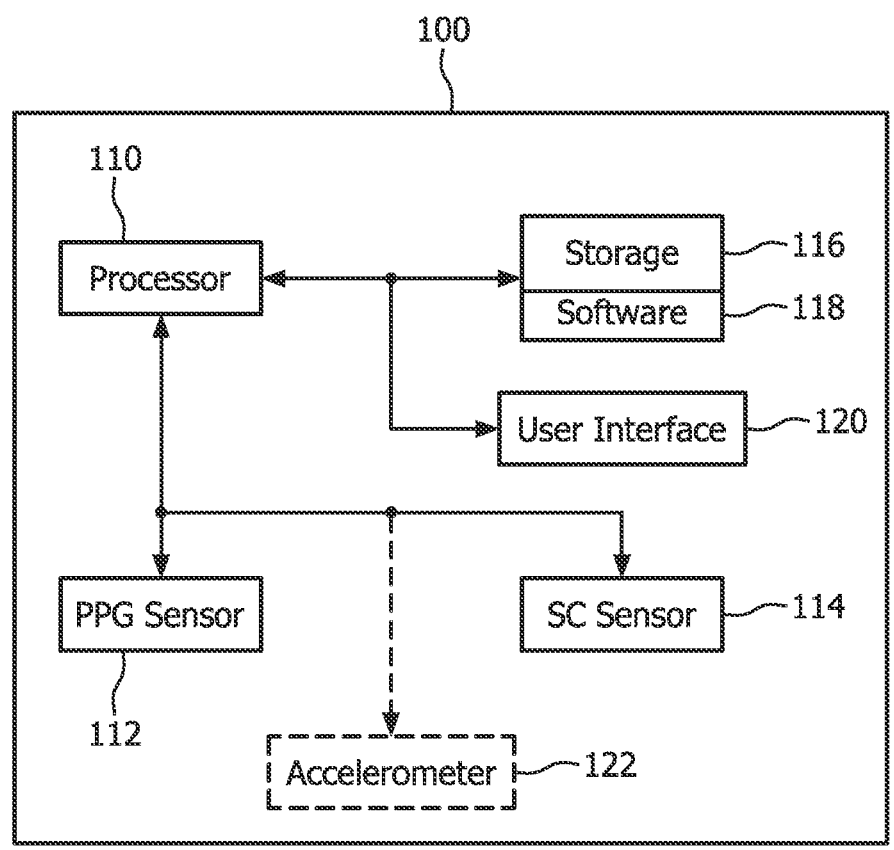
FIG. 1 is a block diagram of a heartbeat detection device.

Various embodiments are described more fully below with reference to the accompanying drawings, which form a part hereof, and which show specific example embodiments. However, the concepts of the present disclosure may be implemented in many different forms and should not be construed as limited to the embodiments set forth herein; rather, these embodiments are provided as part of a thorough and complete disclosure, to fully convey the scope of the concepts, techniques and implementations of the present disclosure to those skilled in the art. Embodiments may be practiced as methods, systems or devices. Accordingly, embodiments may take the form of a hardware implementation, an entirely software implementation or an implementation combining software and hardware aspects. The following detailed description is, therefore, not to be taken in a limiting sense.

Reference in the specification to "one embodiment" or to "an embodiment" means that a particular feature, structure, or characteristic described in connection with the embodiments is included in at least one example implementation or technique in accordance with the present disclosure. The appearances of the phrase "in one embodiment" in various places in the specification are not necessarily all referring to the same embodiment.

Some portions of the description that follow are presented in terms of symbolic representations of operations on non-transient signals stored within a computer memory. These descriptions and representations are used by those skilled in the data processing arts to most effectively convey the substance of their work to others skilled in the art. Such operations typically require physical manipulations of physical quantities. Usually, though not necessarily, these quantities take the form of electrical, magnetic or optical signals capable of being stored, transferred, combined, compared and otherwise manipulated. It is convenient at times, principally for reasons of common usage, to refer to these signals as bits, values, elements, symbols, characters, terms, numbers, or the like. Furthermore, it is also convenient at times, to refer to certain arrangements of steps requiring physical manipulations of physical quantities as modules or code devices, without loss of generality.

However, all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices. Portions of the present disclosure include processes and instructions that may be embodied in software, firmware or hardware, and when embodied in software, may be downloaded to reside on and be operated from different platforms used by a variety of operating systems.

The present disclosure also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each may be coupled to a computer system bus. Furthermore, the computers referred to in the specification may include a single processor or may be architectures employing multiple processor designs for increased computing capability.

The processes and displays presented herein are not inherently related to any particular computer or other apparatus. Various general-purpose systems may also be used with programs in accordance with the teachings herein, or it may prove convenient to construct more specialized apparatus to perform one or more method steps. The structure for a variety of these systems is discussed in the description below. In addition, any particular programming language that is sufficient for achieving the techniques and implementations of the present disclosure may be used. A variety of programming languages may be used to implement the present disclosure as discussed herein.

In addition, the language used in the specification has been principally selected for readability and instructional purposes and may not have been selected to delineate or circumscribe the disclosed subject matter. Accordingly, the present disclosure is intended to be illustrative, and not limiting, of the scope of the concepts discussed herein.

The present disclosure relates to sensors and/or sensing techniques for detecting heart rate (HR) and/or heart rate variability (HRV). Some embodiments of the present disclosure use multiple sensors and/or sensing techniques for sensing heartbeats, which may be used to determine HR and/or HRV. According to some embodiments, one or more skin conductance (SC) sensors are employed, and may be used with one or more photoplethysmograph (PPG) sensors to detect and/or measure heartbeats and/or heart inter-beat intervals of a living subject, such as a mammal, including a human. These embodiments may be wearable and/or portable with the subject. For example, the disclosed methods and apparatuses may be implemented by attachments to a subject's body, including implementation as bands around an appendage, such as wristbands for a human. The methods and apparatuses may be implemented with electronics and/or software, and may be optimized for accurately measuring inter-beat intervals (IBIs) while minimizing power usage. For example, during high activity episodes of the subject, SC may be used to detect heartbeats. During low activity episodes of the subject, photoplethysmography may be used to detect heartbeats. Embodiments discussed herein may alter the operation of one or more sensors to have greater or lesser sensitivity, power usage and/or sensing range. For example, in the case of a PPG sensor, the light output, spectrum or sensitivity of one or more PPG sensors may be modified, such as by being decreased or increased, during periods of low activity. Such modifications may be made while maintaining a certain level of accuracy, and/or without loss of accuracy.

Some embodiments of the present disclosure may include a motion sensor such as, e.g., an accelerometer. The motion sensor may be capable of sensing motion in one or more dimensions. The motion sensor may be used to capture data that may be used to reduce motion artifacts from PPG HR sensing or measurements. Other embodiments may omit such a motion sensor, or forego the use of such a motion sensor. According to some embodiments, a controller may be used to switch from PPG sensing or measurements to SC sensing or measurements when motion artifacts are detected. Motion artifacts may be detected from the signal provided by the PPG sensor.

The SC sensor is adapted to measure skin conductance response rise times, which are a proxy for sensing blood pressure. For example, skin conductance can be used to detect cardiovascular events that can be used to determine blood pressure, including diastolic blood pressure. The SC sensor typically samples skin conductance from tens to hundreds of times per second, with an accuracy of less than one nanoSiemens. In some embodiments, the output of the SC sensor may be filtered with, e.g., a low-pass filter having a cutoff frequency on the order of the sampling rate of the SC sensor.

Referring to FIG. 1, a device 100 for sensing HR and/or HRV is illustrated in block diagram form. Device 100 includes a processor 110, a PPG sensor 112, an SC sensor 114, a storage 116 and a user interface 120. Storage 116 may be any type of media that is usable with device 100, and may store software 118. Software 118 may include instructions that can be executed by processor 110 to implement HR and/or HRV sensing functions, as well as other functions. PPG sensor 112 and SC sensor 114 each may be composed of one or more constituent sensors. Device 100 may optionally include an accelerometer 122, which is shown in dashed lines to indicate that it is optional.

Processor 110 may operate as a controller for PPG sensor 112, SC sensor 114 and/or user interface 120. Processor 110 may receive signals from and send signals to PPG sensor 112, SC sensor 114 and/or user interface 120. For example, processor 110 may receive raw sensor data from PPG sensor 112 and/or SC sensor 114, and/or may receive signals that represent filtered or processed sensor data from these sensors. Processor 110 may store the signals from PPG sensor 112 and/or SC sensor 114 in storage 116. Software 118 may be accessed and used by processor 110 to perform the functions desired with respect to controlling PPG sensor 112 and/or SC sensor 114 and/or processing signals or data, including those used in conjunction with storage 116 and/or user interface 120. Processor 110 may control PPG sensor 112 and/or SC sensor 114 to achieve various functions, including obtaining sensing data, turning on or off functionality within the sensors or turning the sensors on or off. In cases where accelerometer 122 is included in device 100, processor 110 may send signals to and receive signals from accelerometer 122. The signals received from accelerometer 122 may include raw sensor data and/or filtered or processed sensor data. According to an example implementation, data from accelerometer 122 may be used to cause a switch between sensors or to reduce the impact of motion artifacts.

Processor 110 can execute software 118 to cause a change in operation of device 100 based on signals received from PPG sensor 112 and/or SC sensor 114 and/or accelerometer 122. For example, processor 110 can analyze signals from PPG sensor 112 and determine the presence of motion artifacts or the loss of a reliable signal for determining HR and/or HRV. Upon such a determination, processor 110 can disregard signals from PPG sensor 112 in determining HR and/or HRV, and/or can disable output from the sensor, shut PPG sensor 112 off or place it in a low power mode to conserve power. Processor 110 may begin using SC sensor 114 as a primary source for signals used to determine HR and/or HRV, which may include turning SC sensor 114 on, enabling an output of the sensor, changing from low power to high power mode, or any other change or switch operation to utilize signals from SC sensor 114 when PPG sensor 112 may provide an unreliable signal.

The switching operation undertaken by processor 110 is a controlled change in the operation of device 100 to meet design goals. According to an example, the controlled change may be turning one or more of PPG sensor 112 and/or SC sensor 114 on or off, or putting one or more sensors in a low power mode. The controlled change may be selecting which sensor, sensor signal, or sensing technique may be used to detect and/or measure heartbeats. The design goals may be obtaining a high degree of reliability, optimized power consumption, or any other goal with respect to desired operation of device 100.

The switching operation can be implemented according to a number of techniques and/or criteria. According to one example, processor 110 monitors the signals from PPG sensor 112 and/or SC sensor 114 and determines HR and/or HRV from the signals obtained from one or both sensors. Processor 110 can determine when the signals from one or more of PPG sensor 112 and/or SC sensor 114 become unreliable for detecting and/or measuring heartbeats, or unreliable for use in calculating HR and/or HRV. For example, processor 110 can determine when an output signal from PPG sensor 112 may include motion artifacts that may distort the output signal. The determination of reliability of a sensor signal by processor 110 can be achieved by analyzing the signals from the sensors for criteria indicative of poor signal quality or loss of a reliable signal according to the sensing technique that can be used to calculate HR and/or HRV.

Figure 2:
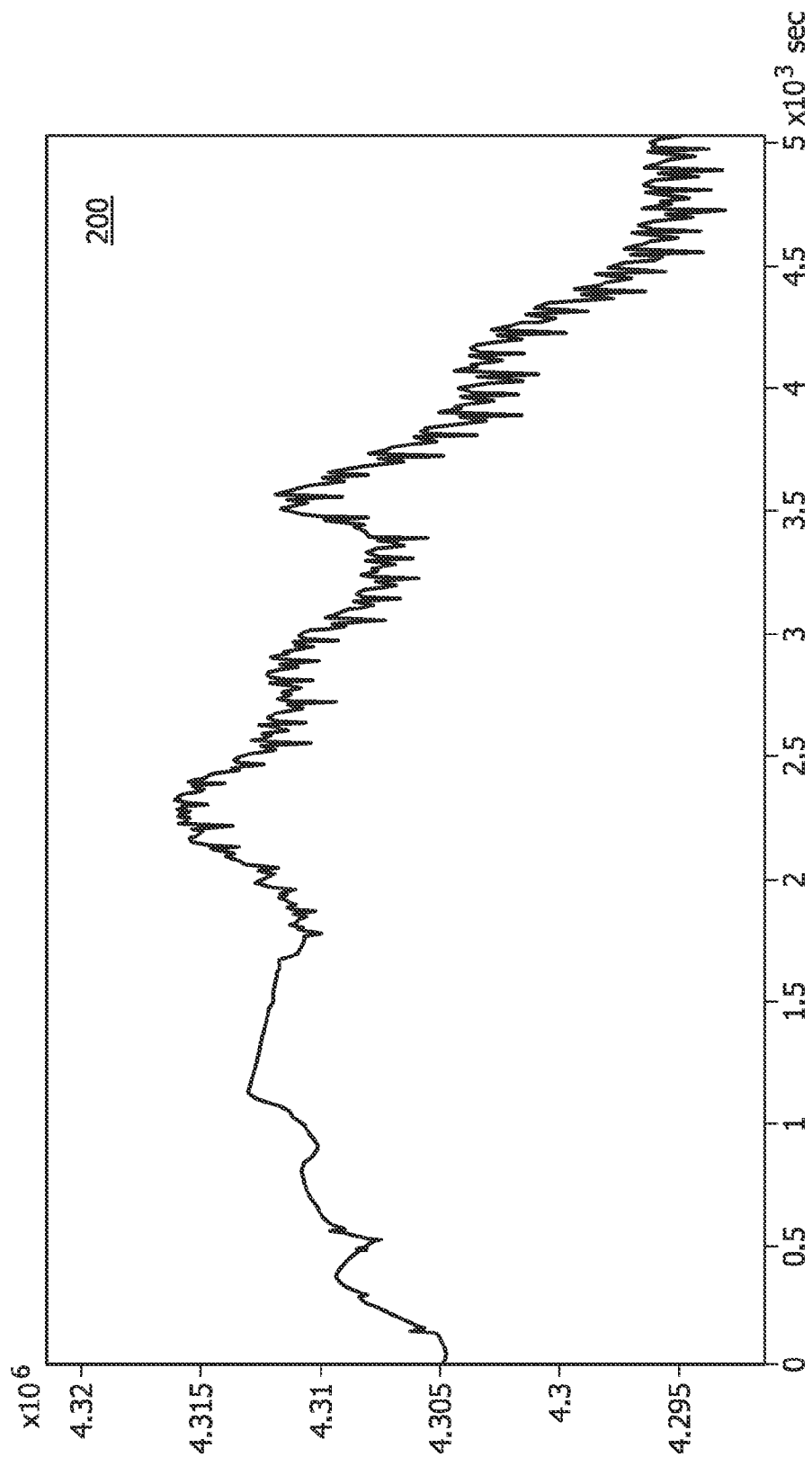
FIG. 2 is a chart of an output of a skin conductance sensor under different stimuli.

Referring to FIG. 2, a trace waveform 200 of an output of a skin conductance sensor is illustrated. Waveform 200 may be obtained from SC sensor 114. From a time period of 0 to 150 on the x-axis, which corresponds to 0 to 15 seconds, the subject to which the skin conductance sensor is applied is at rest. At around 150 on the x-axis, the subject begins to move and walks at a steady pace. A ripple in the signal caused by heartbeats becomes pronounced over the timeframe of about 175 to 500 on the x-axis as the subject continues to move. Processor 110 (FIG. 1) may receive a signal from SC sensor 114, which may represented by waveform 200, and perform processing on the signal to obtain an indication of a heartbeat, from which HR and/or HRV may be determined. Alternatively, or in addition, SC sensor 114 may process a raw sensor signal and provide processor 110 with a signal that represents a heartbeat, when such can be detected by SC sensor 114.

In an example implementation, SC sensor 114 detects and/or measures skin conductance with high precision and at a relatively high rate. SC sensor 114 may be designed with custom sensing electronics that include an anti-aliasing filter and/or a balanced, floating design that may include differential detection and/or measurement. A digital filter may be employed by SC sensor 114 to convert a raw analog signal to a digital signal, which may be implemented with an analog to digital converter. The digital and/or filtered signal includes peaks that are related to heartbeats, and thus represents a signal from which heartbeats can be extracted. HR and/or HRV may be obtained from the timestamps of the peaks.

As the subject to which SC sensor 114 is applied begin to move, e.g., walks, the ripple caused by the subject's heartbeat becomes more pronounced in the output signal of SC sensor 112. A high-pass filter can be applied to the output signal, with a cutoff frequency approximating a normal human heartbeat, e.g. about 1 Hz. This or other filtering may separate the slower skin conductance level variations from the heartbeat events under inspection. Signal processing techniques may be applied to the filtered signal to obtain timestamps of the minima of the heartbeat valleys, which may be use to derive IBIs. The HR and/or HRV can be deduced from the IBIs. The filtering, signal processing, calculations and/or other functions discussed above may be performed by SC sensor 114 or may be performed concurrently or separately by processor 110 or another component or combination of components. The thus obtained data for heartbeats, IBIs, HR and/or HRV can be stored in storage 116 and/or on other mediums, such as a micro SD card. The data may also or alternatively be transmitted via a communication link, such as a wireless link, which may be, for example, a Bluetooth link, to a receiving station, such as a Bluetooth equipped mobile phone.

During low activity periods, such as during sleep cycles, the heart beat attenuation of skin conductance becomes relatively very small. Heartbeats may be detected using skin conductance during such periods, however, the ripple in the sensor signal used to detect heartbeats may be more difficult to detect. During such periods, embodiments of the present disclosure may switch from the use of SC sensor 114 to the use of PPG sensor 112 to determine IBI. This switch may reduce power consumed and may contribute to extending the life of a battery in device 100 or otherwise extend the life of device 100.

PPG sensor 112 may operate in a low power mode when motion artifacts are not present. Typically, PPG sensing reliability may be diminished by being changed in position with respect to the subject being observed. As the subject moves, motion artifacts may appear in an output signal of PPG sensor 112. Thus, when the subject is in motion, corrections or compensation may be applied to remove or diminish the impact of motion artifacts in an output signal of PPG sensor 112. The corrections or compensation may be derived from accelerometer 122, which can detect motion and supply a signal to processor 110 to indicate a time, a direction and/or a magnitude of motion of device 100. When PPG sensor 112 is used with a subject that is not in motion, the corrections or compensation may be unnecessary, thus leading to lower power usage. According to an example implementation, processor 110 analyzes an output signal from PPG sensor 112, and upon detection of motion artifacts, selects an output signal from SC sensor 114 to detect and/or measure heartbeats. Thus, in this example implementation, PPG sensor 112 is used to detect heartbeats when the subject is at rest, and SC sensor 114 is used to detect heartbeats when the subject is in motion.

Other types of switching or changes to the operation of device 100 may be implemented. For example, processor 110 may analyze an output signal from SC sensor 114 and determine the presence or absence of waveform ripples that would be indicative of heartbeats. Such an analysis may be carried out by filtering the output signal as discussed above and detecting peaks or valleys in the filtered signal. In the absence of detection of peaks and/or valleys in the filtered signal, processor 110 may begin using an output signal from PPG sensor 112 to detect heartbeats from the subject. Processor 110 may also turn SC sensor 114 off, or place the sensor in a low power mode.

Figure 3:
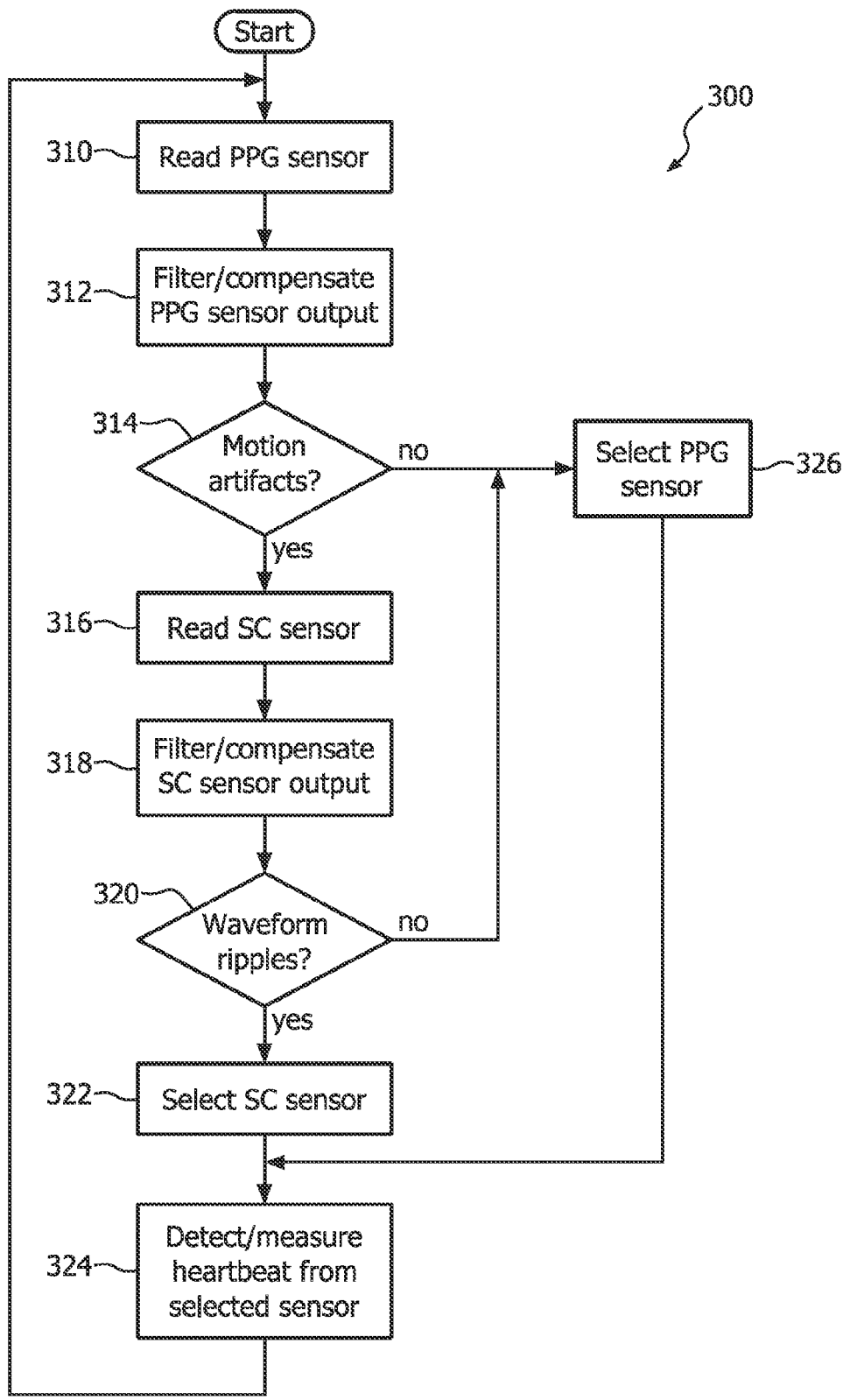
FIG. 3 is a flowchart of a heartbeat detection method.

Referring to FIG. 3, a flowchart 300 illustrates an example process for detecting and/or measuring heartbeats. The process begins with obtaining an output from a PPG sensor, which may be PPG sensor 112, as shown with a block 310. The output of the PPG sensor may be filtered or have some type of compensation applied, such as processing for detecting motion artifacts, as illustrated in a block 312. If motion artifacts are detected in the output of the PPG sensor, the device for detecting heartbeats can change its operation. The determination of whether motion artifacts are detected in the output of the PPG sensor is illustrated with a decision block 314. If no motion artifacts are detected, the PPG sensor is selected for further heartbeat sensing, as illustrated by a block 326 being reached from the No branch from decision block 314.

If motion artifacts are detected in the output of the PPG sensor, the output of an SC sensor is read, as illustrated with a block 316 being reached from a Yes branch of decision block 314. The SC sensor may be implemented as SC sensor 114. The output of the SC sensor may be filtered or have some type of compensation applied, such as processing to detect waveform ripples that may be indicative of heartbeats, as is illustrated in a block 318. The determination of whether the SC censor output includes waveform ripples is illustrated in a decision block 320. If no waveform ripples are detected in the SC sensor output, the PPG sensor is selected for detecting and/or measuring heartbeats, as illustrated with block 326 being reached from the No branch of decision block 320. Otherwise, if waveform ripples are detected in its output, the SC sensor is selected for further heartbeat sensing, as illustrated by a block 322 being reached via the Yes branch of decision block 320. After the selection of the heartbeat sensor, either at block 326 or at block 322, the heartbeat sensing process detects and/or measures the heartbeat from the selected sensor, as illustrated in a block 324. The process continues by looping back to read the PPG sensor, as illustrated with the flowchart path from block 324 2 block 310.

The process illustrated in flowchart 300 may tend to favor use of the PPG sensor, since that sensor is tested first for motion artifacts, as illustrated in decision block 314. According to other examples, the process illustrated in flowchart 300 can be rearranged to cause the SC sensor to be tested first, or concurrently with the PPG sensor. A switch between sensors can be undertaken when motion artifacts, or the lack thereof, are sensed in the output of the PPG sensor, or when waveform ripples, or lack thereof, are sensed in the output of the SC sensor. In addition, the selection of a sensor in the process illustrated in flowchart 300 may be implemented as turning the sensor(s) on, and/or turning the sensor(s) off, or changing from a low-power mode to a high-power mode, or vice versa. For example, selection of the PPG sensor illustrated in block 326 may be implemented by turning off the SC sensor, by placing the SC sensor in a low-power mode or by ignoring the output of the SC sensor for the purpose of detecting and/or measuring heartbeats. Selection of the SC sensor illustrated in block 322 may be implemented by turning off the PPG sensor, by placing the PPG sensor in a low-power mode or by ignoring the output of the PPG sensor for the purpose of detecting and/or measuring heartbeats.

Figure 4:
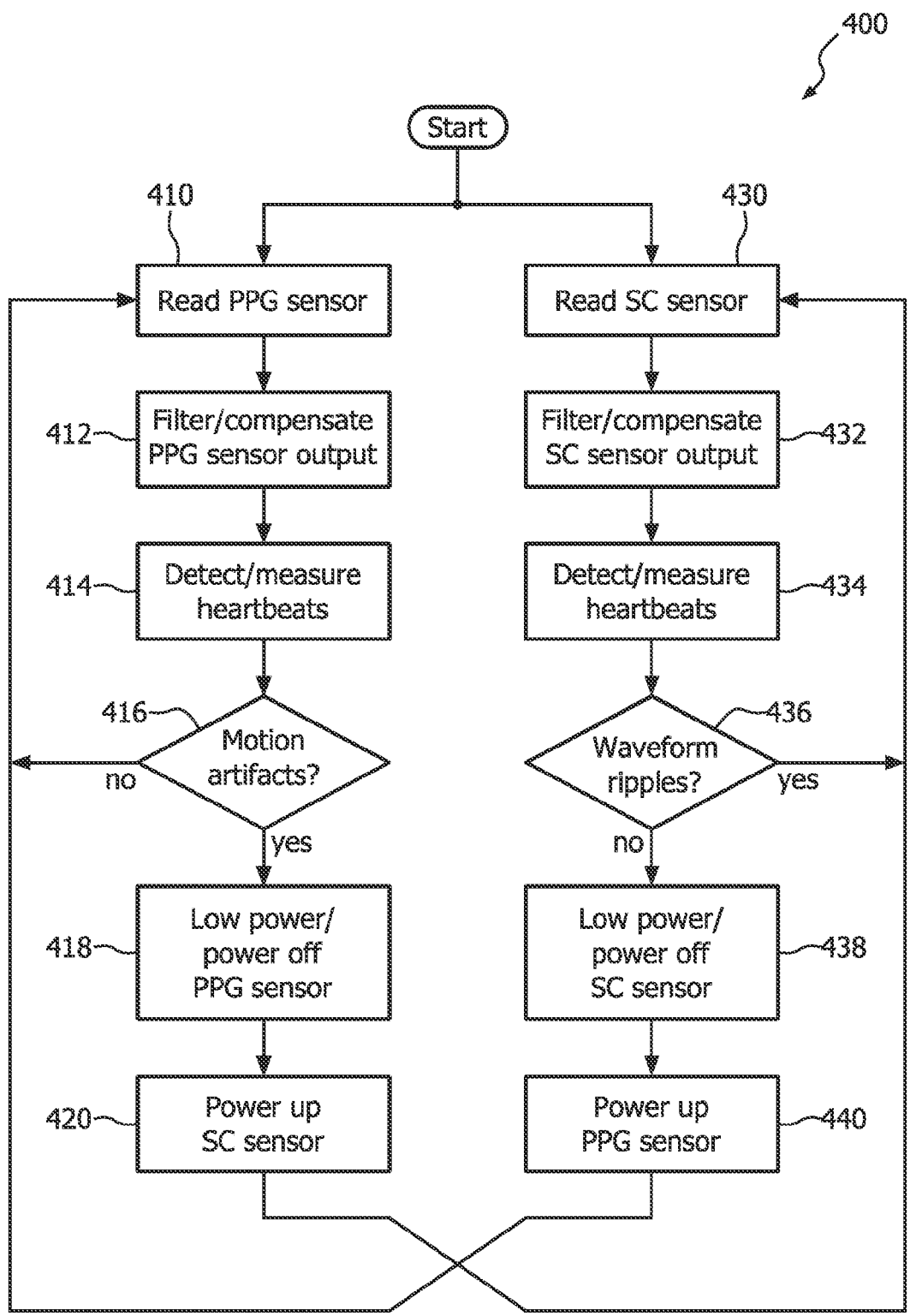
FIG. 4 is a flowchart of a heartbeat detection method.

Referring now to FIG. 4, a flowchart 400 illustrates an example process for detecting and/or measuring heartbeats. The process begins with obtaining an output from a PPG sensor, which may be PPG sensor 112, as shown with a block 410, and obtaining an output from an SC sensor, which may be SC sensor 114, as shown with a block 430. The output of the PPG sensor may be filtered or have some type of compensation applied, such as processing for detecting motion artifacts, as illustrated in a block 412. Detection and/or measurement of heartbeats using the PPG sensor is attempted, as illustrated with a block 414. If motion artifacts are detected in the output of the PPG sensor, the device for detecting heartbeats can change its operation. The determination of whether motion artifacts are detected in the output of the PPG sensor is illustrated with a decision block 416. If no motion artifacts are detected, further heartbeat detection and/or measurement may be made using the PPG sensor, as illustrated by the No branch from decision block 416 being directed back to block 410 to obtain further PPG sensor readings.

When the SC sensor is read, as illustrated with block 430, the output of the SC sensor may be filtered or have some type of compensation applied, such as processing to detect waveform ripples that may be indicative of heartbeats, as is illustrated in a block 432. Detection and/or measurement of heartbeats using the SC sensor is attempted, as illustrated with a block 434. A determination of whether the SC sensor output includes waveform ripples is illustrated in a decision block 434. If waveform ripples are detected, further heartbeat detection and/or measurement may be made using the SC sensor, as illustrated by the Yes branch from a decision block 436 being directed back to block 430 to obtain further SC sensor readings.

If motion artifacts are detected in the output of the PPG sensor, the operation of the heartbeat sensing device can be changed. In the process illustrated in flowchart 400, the PPG sensor is placed in a low-power mode, or powered off, as illustrated with a block 418 being reached from the Yes branch of decision block 416. In addition, the SC sensor is powered up, as illustrated in a block 420. Powering up the SC sensor may be implemented by changing from a low-power mode to a higher power mode, or by turning the sensor on, or by enabling an output of the SC sensor to be used to detect and/or measure heartbeats. Following power up of the SC sensor, the sensor output is read, as illustrated with the path from block 420 to block 430 in flowchart 400.

With respect to the SC sensor, if waveform ripples are not detected in the output of the sensor, the operation of the heartbeat sensing device can be changed. In the process illustrated in flowchart 400, the SC sensor is placed in a low-power mode, or powered off, as illustrated with a block 438 being reached from the No branch of decision block 436. In addition, the PPG sensor is powered up, as illustrated in a block 440. Powering up the PPG sensor may be implemented by changing from a low-power mode to a higher power mode, or by turning the sensor on, or by enabling an output of the PPG sensor to be used to detect and/or measure heartbeats. Following power up of the PPG sensor, the sensor output is read, as illustrated with the path from block 440 to block 410 in flowchart 400.

The process illustrated in flowchart 400 can provide different modes of operation for the heartbeat sensing device, which modes of operation may be implemented in device 100 (FIG. 1). In one mode, when there are no motion artifacts in the output of the PPG sensor and there are waveform ripples in the output of the SC sensor, each sensor can operate independently and concurrently to provide heartbeat data. In a second mode, motion artifacts are observed in the output of the PPG sensor, leading to the PPG sensor being turned off, or being placed in a low-power state, while waveform ripples are observed in the output of the SC sensor, which continues to operate in a normal state. In a third mode, motion artifacts are not observed in the output of the PPG sensor, which continues to operate in a normal state, while waveform ripples are absent from the output of the SC sensor, leading to the SC sensor being turned off, or being placed in a low-power state. In a fourth mode, motion artifacts are observed in the output of the PPG sensor and waveform ripples are absent from the output of the SC sensor, leading to the sensors being alternately switched between being powered up or powered down. This switching state continues either until motion artifacts are not observed in the output of the PPG sensor, or until waveform ripples are observed in the output of the SC sensor. Accordingly, the process illustrated in flowchart 400 uses the output of the sensor that is best able to provide heartbeat data, and switches between the sensors until a better heartbeat data source can be identified.

Figure 5:
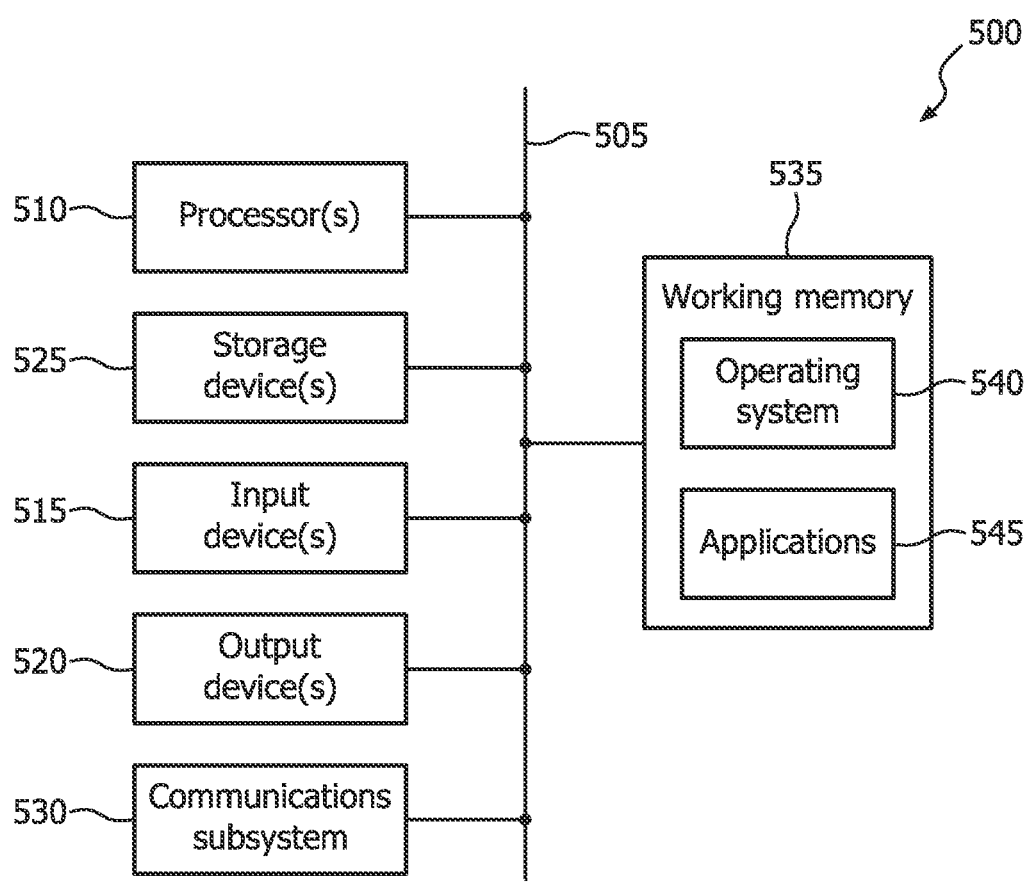
FIG. 5 is a block diagram of a computer system that may be used to implement techniques discussed herein.

A computer system as illustrated in FIG. 5 may incorporate or implement some of the previously described devices or methods. FIG. 5 provides a schematic illustration of one embodiment of a computer system 500 that can perform the methods provided by various other embodiments, as described herein, and/or can function as the host computer system, a remote kiosk/terminal, a point-of-sale device, a mobile device, and/or a computer system. It should be noted that FIG. 5 is meant only to provide a generalized illustration of various components, any or all of which may be utilized as appropriate. FIG. 5, therefore, broadly illustrates how individual system elements may be implemented in a relatively separated or relatively more integrated manner.

The computer system 500 is shown comprising hardware elements that can be electrically coupled via a bus 505 (or may otherwise be in communication, as appropriate). The hardware elements may include one or more processors 510, including without limitation one or more general-purpose processors and/or one or more special-purpose processors (such as digital signal processing chips, graphics acceleration processors, and/or the like); one or more input devices 515, which can include without limitation a mouse, a keyboard and/or the like; and one or more output devices 520, which can include without limitation a display device, a printer and/or the like.

The computer system 500 may further include (and/or be in communication with) one or more non-transitory storage devices 525, which can comprise, without limitation, local and/or network accessible storage, and/or can include, without limitation, a disk drive, a drive array, an optical storage device, solid-state storage device such as a random access memory ("RAM") and/or a read-only memory ("ROM"), which can be programmable, flash-updateable and/or the like. Such storage devices may be configured to implement any appropriate data stores, including without limitation, various file systems, database structures, and/or the like.

The computer system 500 might also include a communications subsystem 530, which can include without limitation a modem, a network card (wireless or wired), an infrared communication device, a wireless communication device and/or chipset (such as a Bluetooth™ device, an 802.11 device, a WiFi device, a WiMax device, cellular communication facilities, etc.), and/or the like. The communications subsystem 530 may permit data to be exchanged with a network (such as the network described below, to name one example), other computer systems, and/or any other devices described herein. In many embodiments, the computer system 500 will further comprise a working memory 535, which can include a RAM or ROM device, as described above.

The computer system 500 also can comprise software elements, shown as being currently located within the working memory 535, including an operating system 540, device drivers, executable libraries, and/or other code, such as one or more application programs 545, which may comprise computer programs provided by various embodiments, and/ or may be designed to implement methods, and/or configure systems, provided by other embodiments, as described herein. Merely by way of example, one or more procedures described with respect to the method(s) discussed above might be implemented as code and/or instructions executable by a computer (and/or a processor within a computer); in an aspect, then, such code and/or instructions can be used to configure and/or adapt a general purpose computer (or other device) to perform one or more operations in accordance with the described methods.

A set of these instructions and/or code might be stored on a computer-readable storage medium, such as the storage device(s) 525 described above. In some cases, the storage medium might be incorporated within a computer system, such as the system 500. In other embodiments, the storage medium might be separate from a computer system (e.g., a removable medium, such as a compact disc), and/or provided in an installation package, such that the storage medium can be used to program, configure and/or adapt a general purpose computer with the instructions/code stored thereon. These instructions might take the form of executable code, which is executable by the computer system 500 and/or might take the form of source and/or installable code, which, upon compilation and/or installation on the computer system 500 (e.g., using any of a variety of generally available compilers, installation programs, compression/decompression utilities, etc.) then takes the form of executable code.

It will be apparent to those skilled in the art that substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

As mentioned above, a computer system (such as the computer system 500) may be employed to perform methods in accordance with various embodiments. According to a set of embodiments, some or all of the procedures of such methods are performed by the computer system 500 in response to processor 510 executing one or more sequences of one or more instructions (which might be incorporated into the operating system 540 and/or other code, such as an application program 545) contained in the working memory 535. Such instructions may be read into the working memory 535 from another computer-readable medium, such as one or more of the storage device(s) 525. Merely by way of example, execution of the sequences of instructions contained in the working memory 535 might cause the processor(s) 510 to perform one or more procedures of the methods described herein.

The terms "machine-readable medium" and "computer-readable medium," as used herein, refer to any medium that participates in providing data that causes a machine to operate in a specific fashion. In some embodiments of the present disclosure, a machine-readable medium contains machine-executable instructions for performing a function, such as a method, for detecting heart rate and/or heart rate variability. In an embodiment implemented using the computer system 500, various computer-readable media might be involved in providing instructions/code to processor(s) 510 for execution and/or might be used to store and/or carry such instructions/code (e.g., as signals). In many implementations, a computer-readable medium is a physical and/or tangible storage medium. Such a medium may take many forms, including but not limited to, non-volatile media, volatile media, and transmission media. Non-volatile media include, for example, optical and/or magnetic disks, such as the storage device(s) 525. Volatile media include, without limitation, dynamic memory, such as the working memory 535. Transmission media include, without limitation, coaxial cables, copper wire and fiber optics, including the wires that comprise the bus 505, as well as the various components of the communication subsystem 530 (and/or the media by which the communications subsystem 530 provides communication with other devices). Hence, transmission media can also take the form of waves (including without limitation radio, acoustic and/or light waves, such as those generated during radio-wave and infrared data communications).

Various forms of computer-readable media may be involved in carrying one or more sequences of one or more instructions to the processor(s) 510 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computer system 500. These signals, which might be in the form of electromagnetic signals, acoustic signals, optical signals and/or the like, are all examples of carrier waves on which instructions can be encoded and that may be employed in some embodiments in accordance with the present disclosure.

The communications subsystem 530 (and/or components thereof) generally will receive the signals, and the bus 505 then might carry the signals (and/or the data, instructions, etc. carried by the signals) to the working memory 535, from which the processor(s) 505 retrieves and executes the instructions. The instructions received by the working memory 535 may optionally be stored on a storage device 525 either before or after execution by the processor(s) 510.

The present application hereby incorporates by reference European patent application no. 14 18 6956 filed on Sep. 30, 2014, the entire disclosure of which is hereby incorporated by reference as if set forth in its entirety herein.

The methods, systems, and devices discussed above are examples. Various configurations may omit, substitute, or add various procedures or components as appropriate. For instance, in alternative configurations, the methods may be performed in an order different from that described, and that various steps may be added, omitted, or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Also, configurations may be described as a process that is depicted as a flow diagram or block diagram. Although each may describe the operations as a sequential process, many of the operations can be performed in parallel or concurrently. In addition, the order of the operations may be rearranged. A process may have additional stages or functions not included in the figure.

A statement that a value exceeds (or is more than) a first threshold value is equivalent to a statement that the value meets or exceeds a second threshold value that is slightly greater than the first threshold value, e.g., the second threshold value being one value higher than the first threshold value in the resolution of a relevant system. A statement that a value is less than (or is within) a first threshold value is equivalent to a statement that the value is less than or equal to a second threshold value that is slightly lower than the first threshold value, e.g., the second threshold value being one value lower than the first threshold value in the resolution of the relevant system.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Having described several example configurations, various modifications, alternative constructions, and equivalents may be used without departing from the spirit of the disclosure. For example, the above elements may be components of a larger system, wherein other rules may take precedence over or otherwise modify the application of various implementations or techniques of the present disclosure. Also, a number of steps may be undertaken before, during, or after the above elements are considered. Accordingly, the above description does not bound the scope of the claims.

Embodiments of the present disclosure, for example, are described above with reference to block diagrams and/or operational illustrations of methods, systems, and computer program products according to embodiments of the present disclosure. The functions/acts noted in the blocks may occur out of the order as shown in any flowchart. For example, two blocks shown in succession may in fact be executed substantially concurrent or the blocks may sometimes be executed in the reverse order, depending upon the functionality/acts involved. Additionally, or alternatively, not all of the blocks shown in any flowchart need to be performed and/or executed. For example, if a given flowchart has five blocks containing functions/acts, it may be the case that only three of the five blocks are performed and/or executed. In this example, any of the three of the five blocks may be performed and/or executed.

The description and illustration of one or more embodiments provided in this application are not intended to limit or restrict the scope of the present disclosure as claimed in any way. The embodiments, examples, and details provided in this application are considered sufficient to convey possession and enable others to make and use the best mode of the claimed embodiments. The claimed embodiments should not be construed as being limited to any embodiment, example, or detail provided in this application. Regardless of whether shown and described in combination or separately, the various features (both structural and methodological) are intended to be selectively included or omitted to produce an embodiment with a particular set of features. Having been provided with the description and illustration of the present application, one skilled in the art may envision variations, modifications, and alternate embodiments falling within the general inventive concept discussed in this application that do not depart from the scope of the accompanying claims.

What is claimed is:

1. An apparatus, comprising:
   a photoplethysmograph sensor configured to detect a heartbeat of a subject and provide a first signal associated with the detected heartbeat;
   a skin conductance sensor configured to detect skin conductance of the subject and provide a second signal associated with the detected skin conductance; and
   a processing unit configured to:
      receive the first and second signals;
      analyze one or more of the first or second signals and determine reliability of the one or more of the first or second signals for use in determinations of heart rate or heart rate variability of the subject, the first and second signals for heart rate or heart rate variability determinations, the analysis of the second signal comprising inspection for waveform ripple; and
      select based on the determined reliability one or more of the first signal or the second signal to determine the heart rate or the heart rate variability of the subject.

2. The apparatus of claim 1, wherein the processing unit is configured to determine the reliability of the first signal based on a determined presence or absence of motion artifacts associated with the first signal.

3. The apparatus of claim 1, wherein the processing unit is configured to determine the reliability of the second signal based on a determined presence or absence of the waveform ripple indicative of a heartbeat and associated with the second signal.

4. The apparatus of claim 1, wherein the processing unit is further configured to apply a digital filter to one or more of the first signal or the second signal.

5. The apparatus of claim 1, wherein the skin conductance sensor is configured to detect skin conductance response times and is responsive to frequencies over 100 Hz.

6. The apparatus of claim 1, wherein the processing unit is further configured to selectively enable or disable one or more of the photoplethysmograph sensor or the skin conductance sensor to manage power consumption.

7. The apparatus of claim 1, further comprising an accelerometer, and wherein the processing unit is configured to enable or disable one or more of the photoplethysmograph sensor or the skin conductance sensor in response to an output of the accelerometer.

8. The apparatus of claim 1, wherein the processing unit is further configured to compute one or more of the heart rate or the heart rate variability from one or more of the first signal or the second signal.

9. The apparatus of claim 1, wherein the processing unit is further configured to switch between use of either the first signal or the second signal for heart rate or heart rate variability determinations based on the determination that the switched-from signal is unreliable.

10. A method, comprising:
    receiving a first signal comprising an indicia of a heartbeat of a subject;
    receiving a second signal comprising skin conductance information for the subject;
    analyzing one or more of the first or second signals and determining reliability of the one or more of the first or second signals for use in determinations of heart rate or heart rate variability of the subject, the first and second signals for heart rate or heart rate variability determinations, the analysis of the second signal comprising inspection for waveform ripple; and
    selecting based on the determined reliability one or more of the first signal or the second signal to determine the heart rate or the heart rate variability of the subject.

11. The method of claim 10, further comprising determining the reliability of the first signal based on a determined presence or absence of motion artifacts associated with the first signal.

12. The method of claim 10, further comprising determining the reliability of the second signal based on a determined presence or absence of the waveform ripple associated with the second signal.

13. The method of claim 10, further comprising digitally filtering one or more of the first signal or the second signal.

14. The method of claim 10, wherein receiving the second signal comprises receiving skin conductance response times with frequencies over 100 Hz.

15. The method of claim 10, further comprising selectively enabling or disabling one or more of a photoplethysmograph sensor or a skin conductance sensor to manage power consumption.

16. The method of claim 10, further comprising receiving motion information, and further comprising enabling or disabling one or more of a photoplethysmograph sensor or a skin conductance sensor in response to an output of the motion information.

17. The method of claim 10, further comprising computing one or more of the heart rate or the heart rate variability from one or more of the first signal or the second signal.

18. The method of claim 10, further comprising switching between use of either the first signal or the second signal for heart rate or heart rate variability determinations based on the determination that the switched-from signal is unreliable.

19. A non-transitory computer readable storage medium comprising executable code that, when executed by a processor unit causes the processor unit to:
    receive a first signal comprising an indicia of a heartbeat of a subject;
    receive a second signal comprising skin conductance information for the subject;
    analyze one or more of the first or second signals and determine reliability of the one or more of the first or second signals for use in determinations of heart rate or heart rate variability of the subject, the first and second signals for heart rate or heart rate variability determinations, the analysis of the second signal comprising inspection for waveform ripple; and
    select based on the determined reliability one or more of the first signal or the second signal to determine the heart rate or the heart rate variability of the subject.

20. The non-transitory computer readable storage medium of claim 19, wherein the executable code, when executed by the processor unit, causes the processor unit to switch between use of either the first signal or the second signal for heart rate or heart rate variability determinations based on the determination that the switched-from signal is unreliable.

* * * * *